(12) United States Patent
Stock et al.

(10) Patent No.: US 8,723,139 B2
(45) Date of Patent: May 13, 2014

(54) SYSTEM AND METHOD FOR AUTOMATICALLY DETERMINING OPTIMAL EXCITATION AND EMISSION WAVELENGTHS OF A FLUOROPHORE

(75) Inventors: Daniel Stock, Hallein-Rif (AT); Michael Katzlinger, Eugendorf (AT)

(73) Assignee: Molecular Devices, LLC, Sunnyvale, CA (US)

( * ) Notice: Subject to any disclaimer, the term of this patent is extended or adjusted under 35 U.S.C. 154(b) by 370 days.

(21) Appl. No.: 13/156,877

(22) Filed: Jun. 9, 2011

(65) Prior Publication Data

US 2012/0313010 A1 Dec. 13, 2012

(51) Int. Cl.
*G01N 21/64* (2006.01)
(52) U.S. Cl.
USPC ................................. 250/458.1; 250/459.1
(58) Field of Classification Search
USPC ........................................ 250/458.1, 459.1
See application file for complete search history.

(56) References Cited

U.S. PATENT DOCUMENTS

| 7,113,285 | B2 | 9/2006 | Katzlinger et al. | |
| 2007/0183931 | A1 | 8/2007 | Stock et al. | |
| 2012/0228519 | A1* | 9/2012 | Gilmore et al. | 250/459.1 |

OTHER PUBLICATIONS

MAXline Microplane Readers, Application Note 30, "Selecting Excitation and Emission Wavelengths Using the SPECTRAmax Gemini Microplate Spectrofluorometer—Basic Principles," Jun. 2010, pp. 1-5.
MAXline Microplane Readers, Application Note 31, "Optimizing Excitation and Emission Wavelengths for Narrow Stokes' Shift Fluorophores Using the SPECTRAmax Gemini and SOFTmax Pro," Jun. 2010, pp. 1-6.

* cited by examiner

*Primary Examiner* — David Porta
*Assistant Examiner* — Kenneth J Malkowski
(74) *Attorney, Agent, or Firm* — Bella Fishman

(57) ABSTRACT

A system for performing spectrofluorometry of a fluorophore sample is provided. The system includes an input module that receives user input corresponding to spectrofluorometer settings. A control module transmits control signals for controlling the spectrofluorometer during respective wavelength scans of a fluorophore sample and a blank sample. The control signals provide for automatic execution of the wavelength scans over an excitation wavelength range and an emission wavelength range. A signal-to-background determination module automatically determines multiple signal-to-background ratios based on fluorescence measurements of the fluorophore sample and the blank sample received from the spectrofluorometer. A signal-to-background analysis module automatically determines the maximum signal-to-background ratio from the multiple signal-to-background ratios.

17 Claims, 5 Drawing Sheets

SYSTEM AND METHOD FOR AUTOMATICALLY DETERMINING OPTIMAL EXCITATION AND EMISSION WAVELENGTHS OF A FLUOROPHORE

FIELD OF THE INVENTION

This invention relates to spectrometers and in particular to spectrofluorometers.

BACKGROUND

Fluorophores are molecular components that cause molecular fluorescence. Fluorophores absorb light energy having one wavelength and emit light energy at a different wavelength. The wavelengths of the absorbed light and the emitted light are commonly and respectively referred to as the excitation wavelength and the emission wavelength. The difference between the wavelengths of the absorbed light and the emitted light is referred to as the Stokes shift. The emission wavelength and the intensity of the emitted energy may depend, for example, on the nature of the fluorophore itself and the surrounding chemical environment.

Researchers may use spectrofluorometers to analyze the fluorescence characteristics of molecular fluorophores. Fluorescence characteristics may include, for example, the intensity of the emitted energy, fluorescence polarization, fluorescence lifetime, and time-resolved fluorescence. Researchers may also analyze the fluorescence characteristics of fluorophores that undergo spectral changes due to varying assay conditions, for example, changes to the intrinsic fluorescence of proteins that depend the three-dimensional folding of the protein.

Spectrofluorometry may involve spectral optimization to identify the excitation-emission wavelength pair that results in the optimal sensitivity level for the fluorophore. Conventionally, researchers may manually set the excitation-emission wavelength settings of the spectrofluorometer to measure fluorescence intensity and manually increment the settings through a desired wavelength range. This approach may be time-consuming and can be prone to error. Further, if a researcher has no prior knowledge of the fluorophore, the researcher may be required to perform a scan across the entire wavelength range in order to identify a wavelength range of interest.

In some situations, researchers may inappropriately select an excitation bandpass and an emission bandpass that are too close together. If the excitation and emission bandpasses are set too close together, crosstalk may result from excitation light leaking into the emission channel. In other circumstances, researchers may set the excitation-emission bandpasses such that the maximum raw intensity results. In either case, the perceived optimal excitation-emission wavelength pair may not result in the optimal sensitivity level for the fluorophore.

Therefore, a need exists for automatically determining the optimal excitation-emission wavelength pair of a fluorophore that results in the optimal sensitivity level for the fluorophore.

SUMMARY

A system for performing spectrofluorometry of a fluorophore sample is provided. The system includes an input module that receives user input corresponding to spectrofluorometer settings. A control module transmits control signals for controlling the spectrofluorometer during respective wavelength scans of a fluorophore sample and a blank sample. The control signals provide for automatic execution of the wavelength scans over an excitation wavelength range and an emission wavelength range. A signal-to-background determination module automatically determines multiple signal-to-background ratios based on fluorescence measurements of the fluorophore sample and the blank sample received from the spectrofluorometer. A signal-to-background analysis module automatically determines the maximum signal-to-background ratio from the multiple signal-to-background ratios.

A computer-implemented method of performing spectrofluorometry of a fluorophore sample is also provided. The computer-implemented method includes prompting for user input that corresponds to spectrofluorometer settings. Control signals are transmitted for controlling a spectrofluorometer during respective wavelength scans of a fluorophore sample and a blank sample. The control signals provide for automatic execution of the wavelength scans over an excitation wavelength range and an emission wavelength range. Multiple signal-to-background ratios are automatically determined based on fluorescence measurements of the fluorophore sample and the blank sample received from the spectrofluorometer. A maximum signal-to-background ratio is automatically determined from the multiple signal-to-background ratios.

A computer program product for performing spectrofluorometry of a fluorophore sample is additionally provided. The computer program product includes instructions that may be executed by a processing module of an electronic system. When the processing module executes the instructions, the computer program product directs the electronic system to prompt for user input that corresponds to spectrofluorometer settings. The computer program product also directs the electronic system to transmit one or more control signals for controlling a spectrofluorometer during respective scans of a fluorophore sample and a blank sample. The control signals provide for automatic execution of the wavelength scans over an excitation wavelength range and an emission wavelength range. The computer program product further directs the electronic system to automatically determine multiple signal-to-background ratios based on fluorescence measurements of a fluorophore sample and a blank sample received from the spectrofluorometer and automatically determine the maximum signal-to-background ratio from the multiple signal-to-background ratios.

BRIEF DESCRIPTION OF THE DRAWINGS

The invention may be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

A computer-implemented system for automatically determining the excitation and emission wavelength pair that results in the optimal sensitivity level for a fluorophore is shown and described. Determining the optimal sensitivity level for a fluorophore includes more than simply identifying the maximum raw intensity of the emitted energy. Determining the optimal sensitivity level for a fluorophore takes into account environmental and observational factors such as, for example, the background and the read time for the sample under test. Accordingly, the optimal sensitivity level for a fluorophore results from the maximum signal-to-background ratio (SB).

Figure 1:
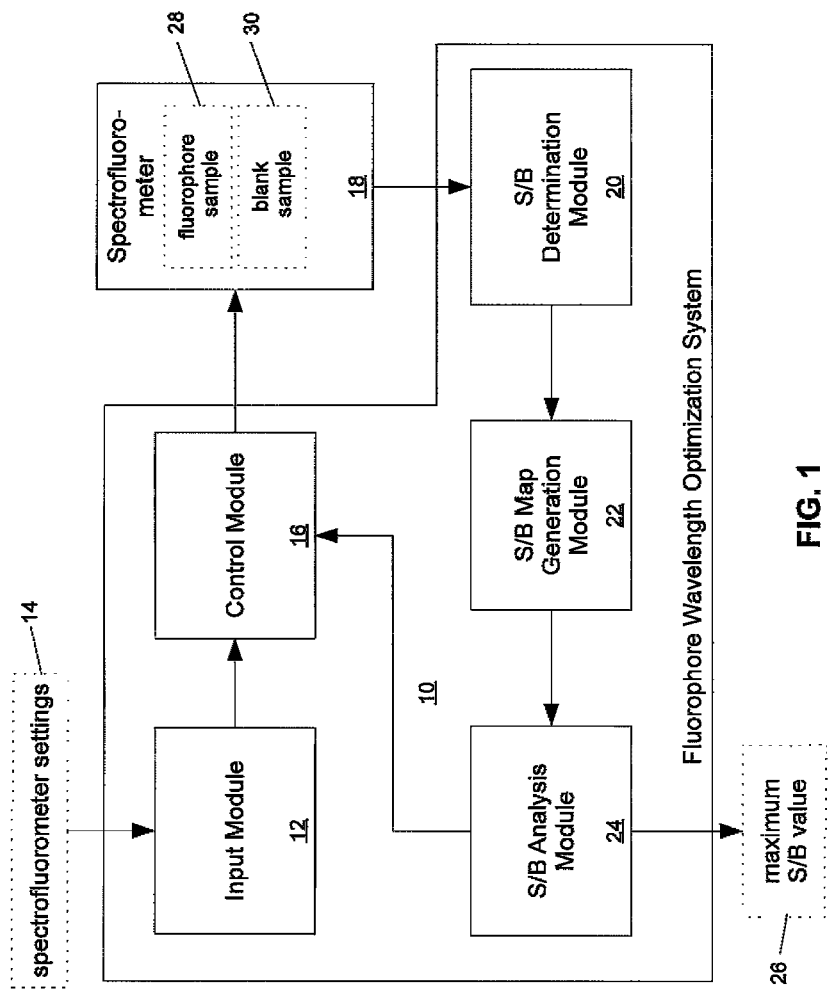
FIG. 1 is an example of an implementation of a system for automatically determining the optimal excitation-emission wavelength pair of a fluorophore.

Referring to FIG. 1, an example implementation of a system 10 for automatically determining the excitation and emission wavelengths of a fluorophore that result in the optimal sensitivity level for the fluorophore is shown. The fluorophore wavelength optimization system 10 in this example includes: a input module 12 for presenting a user interface and for receiving spectrofluorometer settings 14 from a user; a control module 16 for controlling a spectrofluorometer 18 that measures the fluorescence characteristics of a fluorophore; a signal-to-background ratio determination module 20 (SB determination module) that determines SB values resulting from excitation-emission wavelength pairs; a signal-to-background ratio map generation module 22 (SB map generation module) that generates a map of the SB values; and a signal-to-background ratio analysis module 24 (SB analysis module) that determines the maximum SB value 26 that corresponds to the optimal excitation-emission wavelength pair that results in the optimal sensitivity level for the fluorophore. The fluorophore wavelength optimization system 10 may be a computer-implemented system, and the modules 16-24 may be implemented as software modules containing instructions for executing fluorophore wavelength optimization.

The input module 12 of the system 10 may provide, for example, a graphical user interface (GUI) that presents a user with input elements for specifying the spectrofluorometer settings used during spectral optimization of a fluorophore. The user interface of the input module 12 receives the following spectrofluorometer settings 14 from the user for an excitation-emission scan: the excitation wavelength range of interest (ROI); the emission wavelength range of interest, and the wavelength increment. The user interface of the input module 12 may selectively receive additional settings and configuration information.

The excitation and emission wavelength ROIs each include a respective start value and a respective end value specified in nanometers (nm). The wavelength increment is also specified in nanometers. An example excitation wavelength ROI may be 400 nm-450 nm (inclusive); and an example emission wavelength ROI may be 450 nm-550 nm (inclusive). An example wavelength increment may be 2 (two) nm. As discussed further below, the spectrofluorometer 18 measures the fluorescence intensity of a fluorophore across the specified excitation and emission wavelength ROIs.

The system 10 may present the user interface of the input module 12 as part of a software-based "wizard," macro, or script in which various user interface displays (FIGS. 3A-C) prompt the user for the spectrofluorometer settings 14 and configuration information. The user input elements of a user interface display may include, but are not limited to, for example: menus, buttons, checkboxes, radio buttons, combo boxes, textboxes, drop-down lists, list boxes, sliders, spinners, icons, data grids, hyperlinks, and the like. It will also be understood that the input module 12 may selectively provide a command-line interface, touch user interface, or any other type of user interface adapted to receive spectrofluorometer settings and configuration information via one or more suitable user input elements.

The control module 16 is in signal communication with the input module 12 and the spectrofluorometer 18. The control module 16 receives the spectrofluorometer settings 14 and configuration information from the input module 12. The control module 16 then generates control signals for controlling the spectrofluorometer 18 during an excitation-emission scan of the fluorophore. In this way, the system 10 automatically scans the fluorophore over the specified excitation and emission wavelength ranges incrementing the excitation and emission wavelengths during iterations of the scan.

The control module 16 pairs each excitation wavelength in the excitation wavelength range with each emission wavelength in the wavelength range for the automatic excitation-emission scan. For each excitation-emission wavelength pair, the control module 16 transmits a control signal to the spectrofluorometer 18 that instructs the spectrofluorometer to measure the fluorescence intensity of the fluorophore at the specified excitation-emission wavelength pair.

Using the example above, an excitation wavelength range may be 400 nm-450 nm, an emission wavelength range may be 450 nm-550 nm, and a wavelength increment may be 2 nm. In this example, there are 26 excitation wavelengths (i.e., 400 nm, 402 nm, . . . , 450 nm) and 51 emission wavelengths (i.e., 450 nm, 452 nm, . . . , 550 nm). The control module 16 pairs each excitation wavelength with each emission wavelength: the control module pairs the 400 nm excitation wavelength with each of the 51 emission wavelengths, pairs the 402 nm excitation wavelength with each of the 51 emission wavelengths, etc. resulting in 1326 total wavelength pairs in this example.

For each wavelength pair, the control module 16 generates a control signal that specifies the excitation-emission wavelength pair (e.g., [400 nm, 450 nm], [400 nm, 452 nm], . . . , [450 nm, 548 nm], [450 nm, 550 nm]) and transmits the control signal to the spectrofluorometer 18. In response, the spectrofluorometer 18 measures the fluorescence intensity of a sample at the excitation wavelength and emission wavelength specified in the control signal. As discussed further below, the spectrofluorometer 18 generates a measurement value that quantifies the fluorescence intensity of a sample at the excitation-emission wavelength pair.

As mentioned above, the optimal sensitivity level for a fluorophore results from the excitation-emission wavelength pair that corresponds to the maximum signal-to-background ratio. Accordingly, the system 10 in the example shown performs an excitation-emission scan on both a fluorophore sample and a blank sample. As seen in FIG. 1, the spectrofluorometer 18 in the example shown includes both a fluorophore sample 28 and a blank sample 30. The control module 16 in the example shown may first perform an excitation-emission scan of the blank sample 30 over the excitation and emission wavelength ranges. The control module 16 may then perform an excitation-emission scan of the fluorophore sample 28 over the excitation and emission wavelength ranges. Continuing with the example above, the control module 16 may perform a first excitation-emission scan of the blank sample 30 over an excitation wavelength range of 400 nm-450 nm and an emission wavelength range of 450 nm-550 nm. The control module 16 may then perform a second excitation-emission scan of the fluorophore sample 28 over the same excitation and emission wavelength ranges, 400 nm-450 nm and 450 nm-550 nm respectively. As discussed further below, the measurements of the fluorophore sample 28 may be corrected using the measurements of the blank sample 30 to obtain the signal-to-background ratio.

The control module 16 may be, for example, a digital control module that generates digital control signals for the spectrofluorometer 18. The control module 16 may interface with the spectrofluorometer 18 via, for example, an RS-232 serial cable or a Universal Serial Bus (USB) cable that couples the control module to the spectrofluorometer. It will be understood that the control module 16 of the system 10 may interface and communicate with the spectrofluorometer 18 via one or a combination of wired or wireless technologies that utilize one or a combination of signal transmission protocols.

The spectrofluorometer 18 receives the control signals from the control module 16 and measures the fluorescence intensity of the fluorophore sample 28 and the blank sample 30 at the excitation and emission wavelengths specified in the control signal. Fluorescence intensity may be quantified in relative fluorescence units (RFUs). The spectrofluorometer 18 may provide an RFU measurement for each excitation-emission wavelength pair. A suitable spectrofluorometer may be, for example, a SpectraMax® Paradigm® Multi-Mode Microplate Detection Platform using, for example, a SpectraMax® Paradigm® Tunable Wavelength (TUNE) Detection Cartridge, which may be available from Molecular Devices, Inc. of Sunnyvale, Calif. Other example spectrofluorometers or other cartridge types may be selectively used.

The SB determination module 20 determines the SB values for each of the excitation-emission wavelength pairs. The SB values are based on the fluorophore measurements (F) and the blank measurements (B). The fluorophore measurements, F, and the blank measurements, B, may be given in RFUs. In order to normalize the fluorophore measurements, the SB determination module 20 reduces the fluorophore measurements, F, by the blank measurements, B, and divides the reduced fluorophore measurements by the blank measurements. Accordingly, the SB determination module 20 may determine the SB values for each excitation-emission wavelength pair using the following formula:

$$SB = \frac{F - B}{B}$$

Accordingly, the system 10 compiles a set of SB values for each excitation-emission wavelength pair across the excitation and emission wavelength ranges. The maximum SB value corresponds to the excitation-emission wavelength pair that results in the optimal sensitivity level for the fluorophore.

Figure 3A:
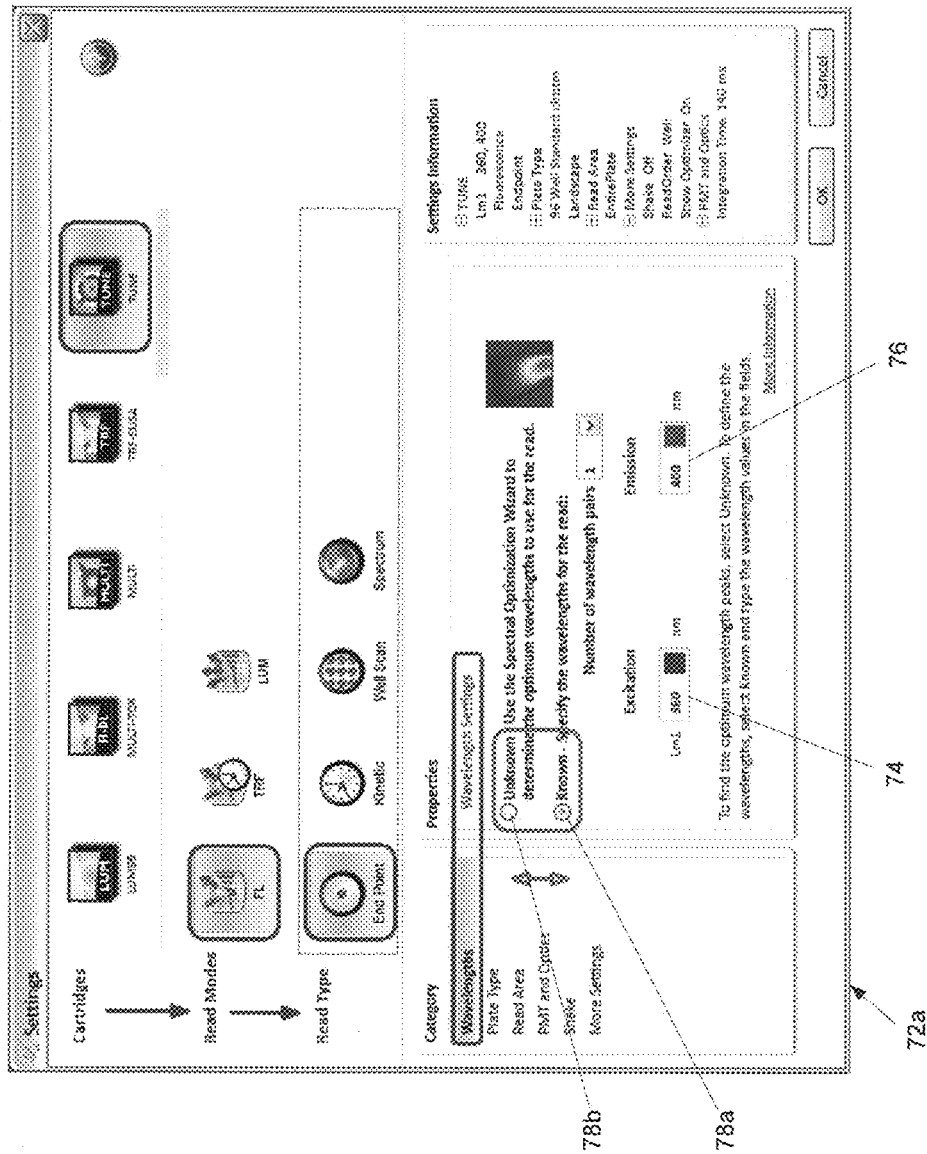
FIG. 3A is an example of a user interface display of a system for automatically determining the optimal excitation-emission wavelength pair of a fluorophore.
Figure 3B:
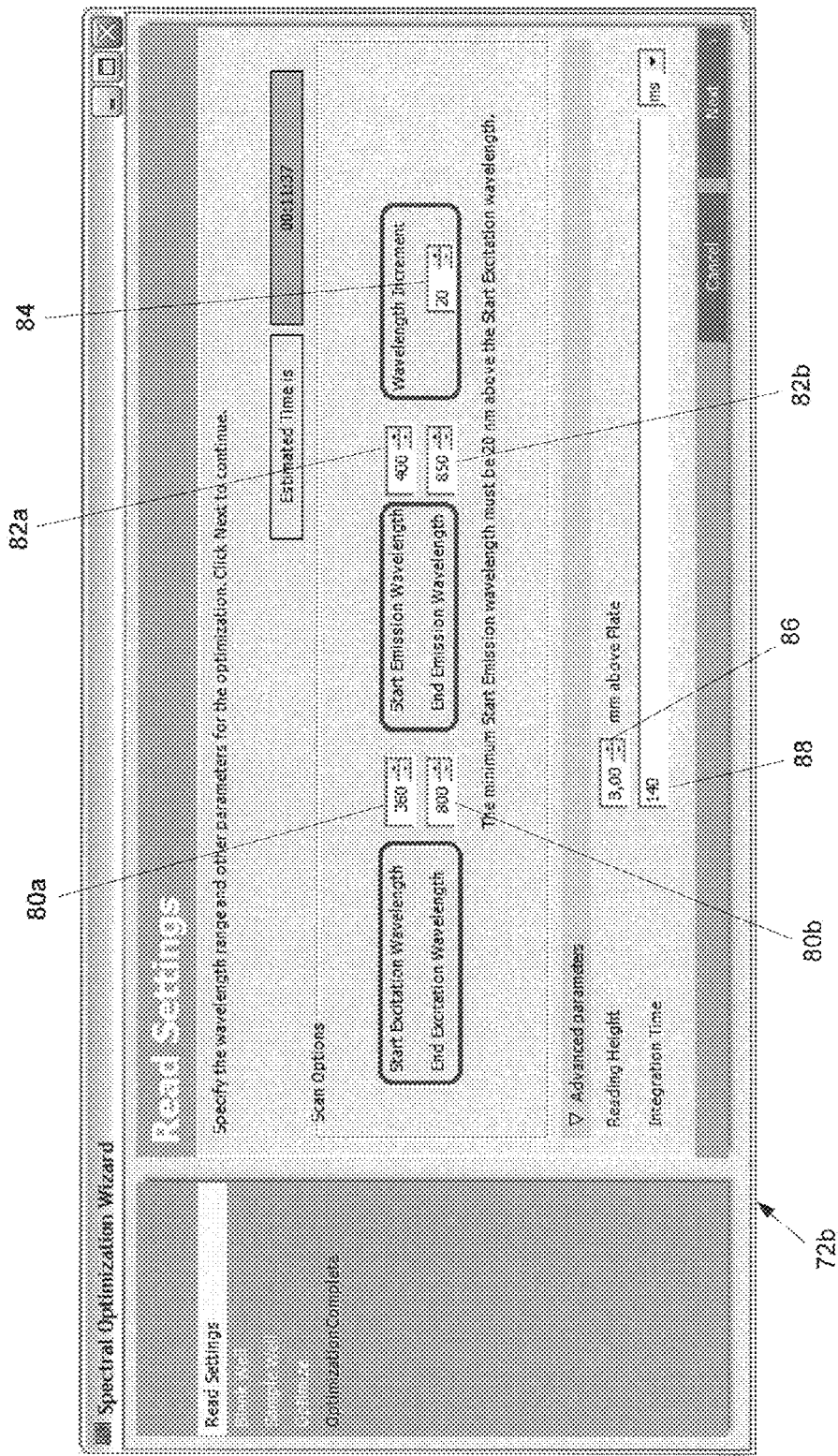
FIG. 3B is an example of a second user interface display of a system for automatically determining the optimal excitation-emission wavelength pair of a fluorophore.
Figure 3C:
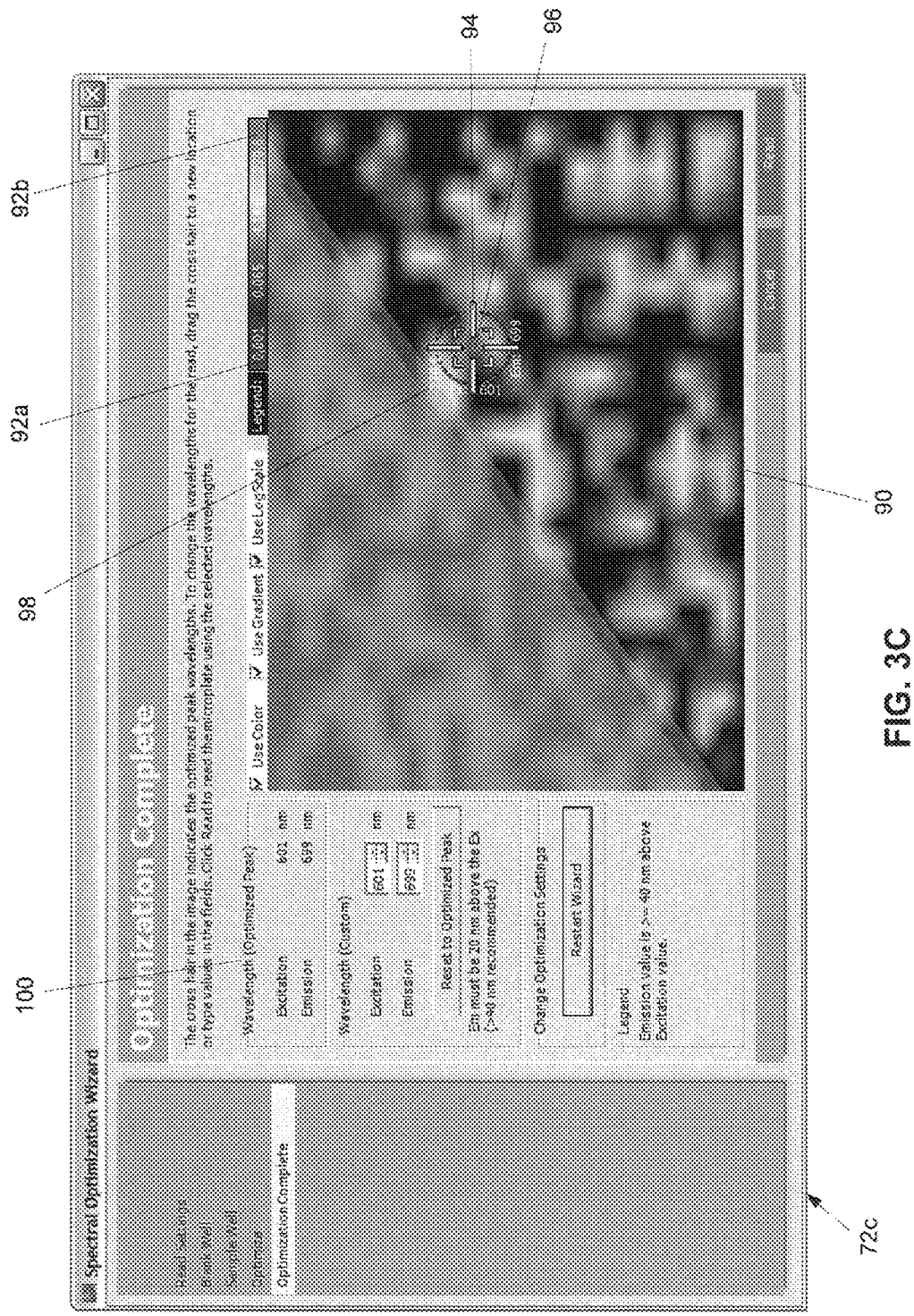
FIG. 3C is an example of a third user interface display of a system for automatically determining the optimal excitation-emission wavelength pair of a fluorophore.

The system 10, in the example shown, includes an SB map generation module 22 for representing the SB values on a map. In this example, the SB map generation module 22 generates a "heat map" in which the SB values are represented as colors on the map. The SB map generation module 22 in the example shown receives the SB values from the SB determination module 20 and maps each SB value to an RGB (red-green-blue) value. For example, relatively low SB values may correspond to bluish and greenish colors and relatively high SB values may correspond to yellowish and reddish colors. The SB map generation module 22 may plot the colors corresponding to the SB values on a two-dimensional graph (i.e., the heat map) in which the vertical axis corresponds to the excitation wavelengths and the horizontal axis corresponds to the emission wavelengths. Accordingly, a user may inspect the heat map and identify the approximate location in the heat map that corresponds to the maximum SB value based on the color of the location. Further, the user may be able to identify the approximate excitation and emission wavelengths that correspond to the maximum SB value based on the position of the location relative to the vertical and horizontal axes. As discussed further below, the system 10 may present the heat map to the user on one of the user interface screens (FIG. 3C).

Additional or alternative approaches for presenting the SB values on a 2D map may be selectively employed. For example, instead of a color-coded heat map that represents the SB values as colors, the SB map generation module 22 may generate a contour map that represents the SB values as contour lines or three-dimensional (3D) surface plots. Contour lines or 3D surface plots may advantageously provide a graphical topography of SB values in which the slopes (or steepness) of various areas in the map indicate the rate of change of the SB values, e.g., whether the SB values around the maximum SB value change slightly or drastically.

The system 10, in the example shown, also includes an SB analysis module 24 to identify the maximum SB value 26. The SB analysis module 24 in the example shown receives the map of SB values from the SB map generation module 22 and analyzes the map to determine the maximum SB value 26. The SB analysis module 24 also determines the excitation-emission wavelength pair associated with the maximum SB value 26. The excitation-emission wavelength pair associated with the maximum SB value corresponds to the optimal sensitivity level for the fluorophore. The SB analysis module 24 may determine the maximum SB value 26 and associated excitation-emission wavelength pair by calculating the absolute maximum of the SB values. The SB analysis module 24 may minimize any noise in the map of SB values by first smoothing the data points used to generate the map.

In the approach set forth above, the system 10 may determine and recommend the excitation and emission wavelength ROIs, and the user may accept or modify the recommend excitation and emission wavelength ROIs to use in the excitation-emission scan. In some circumstances a user may have enough prior knowledge of the fluorophore to specify the excitation and emission wavelength ROIs for the excitation-emission scan. For example, a user may have information relating to the approximate excitation and emission wavelength peak positions for the fluorophore. The wavelength peak positions of the fluorophore allow a user to narrow down the excitation and emission wavelength ROIs. A user may set the start value for a wavelength ROI below (e.g., approximately 50 nm below) the wavelength peak and set the end value of a wavelength ROI above (e.g., approximately 50 nm above) the wavelength peak. For example, if the wavelength peak for the excitation wavelength is 450 nm, a user may set the excitation wavelength ROI as 400 nm-500 nm.

In other circumstances however, a user may not have enough prior knowledge of the fluorophore to identify the excitation and emission wavelength ROIs. As a result, the user may scan the entire wavelength range accessible by the spectrofluorometer to narrow down and identify the excitation and emission ROIs. Scanning the entire wavelength range accessible by the spectrofluorometer, however, may take a relatively longer amount of time than scanning a relatively narrower wavelength ROIs. Therefore, it may be advantageous to first identify an excitation wavelength ROI and emission wavelength ROI to reduce the time it takes to perform the excitation-emission scan.

The system 10 may automatically determine and recommend excitation and emission wavelength ROIs by executing an automatic "low-resolution" pre-scan of the fluorophore over the entire accessible wavelength range. The system 10 may then execute a "high-resolution" scan of the fluorophore over the excitation and emission ROIs identified in the low-resolution pre-scan. "Low-resolution" and "high-resolution" refer to the size of the wavelength increments used during the respective low-resolution and high-resolution scans. The high-resolution wavelength increment is relatively smaller than the wavelength increment for the low resolution scan.

The wavelength increment for the low-resolution scan may be selected based on, for example, the bandwidth of the spectrofluorometer or the bandwidth of the fluorophore. Spectrofluorometers may have different bandwidths: some may resolve at approximately 10 nm while others may resolve down to 1 or 2 nm. In some implementations, the wavelength increment for the low-resolution scan may be selected, for example, from the greater of the spectrofluorometer half-bandwidth and the fluorophore half-bandwidth. For fluorophores used as labels in biopharmaceuticals, a wavelength increment for a low-resolution scan may be, for example, in the range of approximately 10-20 nm.

The wavelength increment for the high-resolution scan may be selected relative to the wavelength increment for the low-resolution scan. For example, the high-resolution wavelength increment may be approximately ten times (10×) smaller than the low-resolution wavelength increment. If a low-resolution wavelength is selected as 20 nm, then a high-resolution wavelength may be selected, for example, as 2 nm.

The low-resolution scan results in a set of preliminary signal-to-background ratio (SB) data. The preliminary SB data may be determined according to the approach set forth above. The system 10 may recommend the excitation and emission wavelength ROIs for the subsequent high-resolution scan based on the excitation and emission wavelengths that correspond to the maximum SB value in the preliminary SB data (e.g., start and end ROI values respectively above and below the wavelength corresponding to the maximum SB value in the preliminary SB data). The system 10 may present the recommended excitation and emission ROIs to the user, and the user may accept or modify the recommended wavelength ROIs.

Additionally or alternatively, the SB map generation module 22 may generate a preliminary map of the preliminary SB values. The SB map generation module may only render SB values in the preliminary SB data that are above a predetermined threshold. For example, the SB map generation module may only render SB values in the map that are higher than 50% of the maximum SB value in the preliminary SB data. The system 10 may present the preliminary map of thresholded SB values to the user, and the user may utilize the information presented in the preliminary SB map to modify the recommended wavelength ROIs to use in a subsequent high-resolution scan of the fluorophore.

In this way, the system 10 does not rely on a user having prior knowledge of the fluorophore. The system 10 can automatically and relatively quickly identify the excitation and emission wavelength ROIs by performing a pre-scan. Once an excitation wavelength ROI and an emission wavelength ROI has been identified—either specified by the user or automatically determined by the system 10—the control module 16 may perform a high-resolution scan (i.e., relatively small wavelength increment) over the identified wavelength ROIs as discussed above.

The system 10 may also quantify the measurement precision (or "instrument sensitivity") at the wavelengths surrounding the maximum SB value by instructing the spectrofluorometer 18 to take repeated measurements of the blank sample and then determining a signal-to-noise ratio (SN). The signal-to-noise ratio relates to background noise that may be present in the measurement value of the blank sample 30. Noise in the blank sample 30 may affect, for example, the readings of diluted fluorophore samples at the corresponding excitation and emission wavelengths. The presence of noise in the blank sample may depend on, for example, the read time per sample and other instrument parameters.

For example, if the heat map shows a relatively more pronounced maximum SB peak, deviations from the optimum wavelength settings (i.e., the excitation and emission wavelengths that correspond to the maximum SB value) may result in a relatively large decrease in fluorescence sensitivity. On the other hand, if the heat map shows a relatively less pronounced maximum SB peak, deviations from the optimum wavelength settings that correspond to the maximum SB value may result in a relatively smaller decrease in fluorescence sensitivity. The topography of the SB value map qualitatively indicates changes in fluorescence sensitivity with the optimum sensitivity located at the maximum SB value. Comparatively, the SN values quantify the degree to which fluorescence sensitivity may decrease when using non-optimum excitation-emission wavelength settings. In some circumstances, a qualitative assessment of the excitation-emission wavelength pairs in the map may be sufficient to choose the wavelength pair that corresponds to the maximum SB value regardless of the slope (or rate of change) surrounding the maximum SB value. In other circumstances, however, there may be reasons not to select the optimum wavelength pair such as, for example, when analyzing compound interference. In circumstances where a user selects a non-optimum wavelength pair, the SN values quantify how much sensitivity may be lost by selecting the non-optimum wavelength pair.

To assess the noise in the blank sample 30, the control module 16 may transmit control signals to the spectrofluorometer 18 that instruct the spectrofluorometer to take—for each excitation-emission wavelength pair—repeated measurements of the blank sample 30 for a predetermined number of cycles. The control signals may specify the number of cycles the spectrofluorometer 18 should perform to obtain the repeated measurements. The number of cycles used to assess background noise may depend on, for example, the read time of each reading of the blank sample 30. In some circumstances, the number of cycles for obtaining repeated measurements may be 20 or more.

Continuing the example above, if the number of cycles is twenty (20), the spectrofluorometer 18 scans the blank sample 30 twenty times at the [400 nm, 450 nm] excitation-emission wavelength pair, and twenty times for each of the subsequent wavelength pairs in the wavelength ranges. The standard deviation of the repeated measurements of the blank sample 30 may be used when determining the signal-to-noise ratio (SN) of the excitation-emission wavelength pair. The SB determination module 20 determines the signal-to-noise ratio by dividing the reduced fluorophore measurements, F, by the standard deviation of the repeated blank measurements, B. Accordingly, the SB determination module 20 may determine the SN value using the following formula:

$$SN = \frac{F - B}{STDEV(B)},$$

where STDEV is a function for calculating standard deviation.

When determining the signal-to-noise ratio, the system 10 may instruct the spectrofluorometer 18 to obtain the repeated measurements of the blank sample during an excitation-emission scan of a fluorophore. Alternatively, the system 10 may instruct the spectrofluorometer 18 to obtain the repeated measurements of the blank sample after the determination of the maximum SB value. Where the repeated measurements are taken after the determination of the maximum SB value, the system 10 may confine the scan of the blank sample to a excitation and emission wavelength regions that are plus-or-minus a few (e.g., two or three) instrument bandwidths away from the optimum wavelength settings. Obtaining the repeated measurements after the determination of the maximum SB value and confining the scan of the blank sample to relatively smaller wavelength regions around the optimum wavelength settings may take less time than obtaining the repeated measurements during an excitation-emission scan of the fluorophore.

Figure 2:
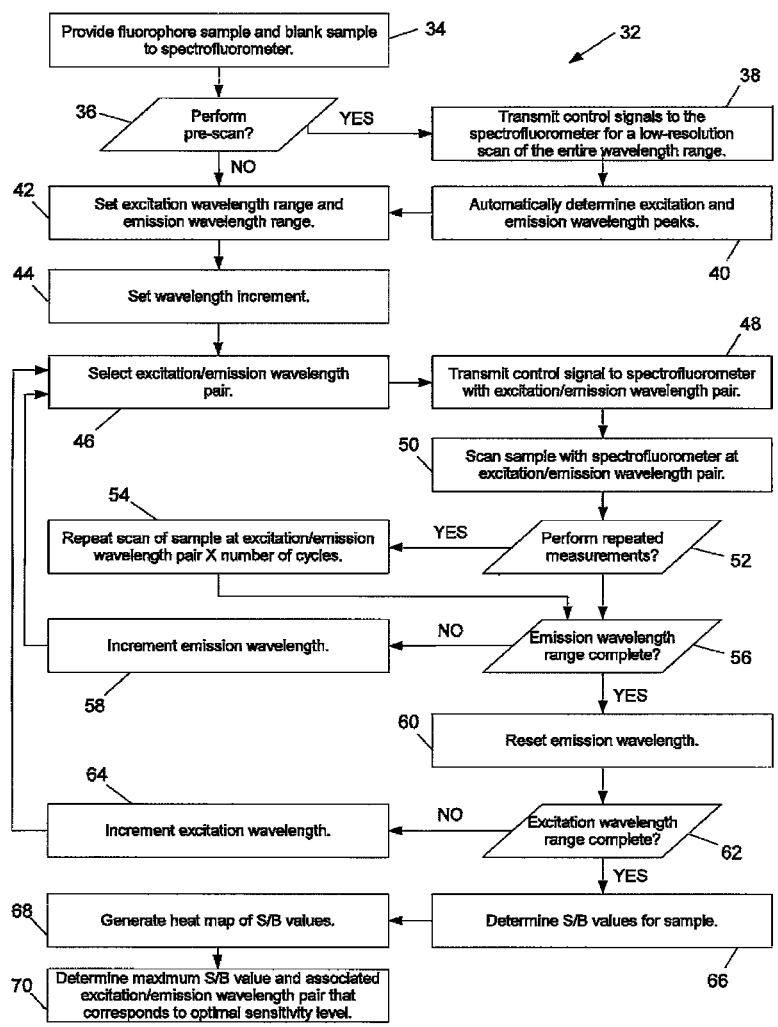
FIG. 2 is an example flowchart illustrating an example process for automatically determining the optimal excitation-emission wavelength pair of a fluorophore.

Referring now to FIG. 2, flowchart 32 illustrating an example process for automatically determining the optimal excitation-emission wavelength pair of a fluorophore is shown. At step 34, a spectrofluorometer is provided with a fluorophore sample and a blank sample to analyze. At step 36, a pre-scan of the fluorophore sample may be performed to identify a range of interest for the excitation range and a range of interest for the emission wavelength range. If the pre-scan is performed, control signals are transmitted to the spectrofluorometer at step 38 that instruct the spectrofluorometer to perform a low-resolution scan of the entire wavelength range. Based on the measurements obtained during the low-resolution scan, the low resolution approximation of the excitation and emission wavelength peaks are automatically determined at step 40. The pre-scan may be used to determine a wavelength range of interest over which to perform the high-resolution excitation-emission scan as discussed above.

The excitation wavelength range and the emission wavelength range for the high-resolution scan is set at step 42, and the wavelength increment is set at step 44. As discussed above, a user may be prompted by a "wizard," macro, or script to input the excitation wavelength ranges, emission wavelength range, and wavelength increment via a user interface. The excitation and emission wavelength ranges may also be set automatically based on the excitation and emission wavelength peaks identified during the pre-scan.

As discussed above, both the fluorophore sample and the blank sample may be automatically scanned across the excitation and emission wavelength ranges. Accordingly, it will be understood that steps 46-64 may be repeated to scan both the fluorophore sample and the blank sample.

At step 46, an excitation-emission wavelength pair is selected. The spectrofluorometer incrementally scans a sample across the specified excitation and emission wavelength ranges automatically incrementing the excitation and emission wavelengths throughout iterations of the scan. For example, the excitation and emission wavelength ranges may be respectively set to 400 nm-450 nm and 450 nm-550 nm, and the wavelength increment may be 2 (two) nm. For each iteration of an excitation wavelength, the spectrofluorometer scans the sample across the entire emission wavelength range automatically incrementing the emission wavelength by the wavelength increment (e.g., [400 nm, 450 nm], [400 nm, 452 nm], . . . , [400 nm, 550 nm], . . . , [402 nm, 450 nm], [402 nm, 452 nm], . . . , [402 nm, 550 nm], . . . , [450 nm, 450 nm], [450 nm, 452 nm], . . . , [450 nm, 550 nm]). After the spectrofluorometer completes a full scan of the emission wavelength range, the emission wavelength is reset (e.g., back to 450 nm) and the excitation wavelength is incremented by the wavelength increment (e.g., from 400 nm to 402 nm).

A control signal includes the selected excitation-emission wavelength pair and is transmitted to the spectrofluorometer at step 48. In response to receipt of the control signal, the spectrofluorometer, at step 50, scans the sample at the specified excitation and emission wavelengths. Repeated measurements of the blank sample may also be taken in order to assess noise in the measurement value of the blank sample. If control signal includes an instruction to take repeated measurements of the blank sample (step 52), the spectrofluorometer repeats the scan of the blank sample at the specified excitation and emission wavelengths at step 54. The control signal may specify the number of cycles (X) for which the spectrofluorometer should repeat the scan. For example, if the control signal specifies that the number of cycles is twenty (20), the spectrofluorometer repeats the scan of the blank sample at the specified excitation and emission wavelength twenty times.

After the spectrofluorometer completes the scan of the sample, it is determined, at step 56, whether the entire emission wavelength range has been scanned. If the sample has not been scanned at an excitation wavelength across the entire emission wavelength range, the emission wavelength is automatically incremented by the wavelength increment (e.g., from 450 nm to 452 nm) at step 58. A new excitation-emission wavelength pair is selected at step 46 that includes the current excitation wavelength and the newly incremented emission wavelength (e.g., [400 nm, 452 nm]). The scan of the sample is then repeated at steps 48-56 using the new excitation-emission wavelength pair.

If the sample has been scanned at an excitation wavelength across the entire emission wavelength range, the emission wavelength is reset at step 60, (e.g., back to 450 nm). Then, it is determined at step 62 if the entire excitation wavelength range has been scanned. If the entire excitation wavelength range has not been scanned, the excitation wavelength is incremented by the wavelength increment (e.g., from 400 nm to 402 nm) at step 64. A new wavelength pair is again selected at step 46 that includes the newly incremented excitation wavelength (e.g., [402 nm, 450 nm]), and the scan of the sample across the emission wavelength range is repeated at steps 48-58. As mentioned above, steps 46-64 are repeated to scan both the fluorophore sample and the blank sample. It will be understood that the order in which the samples are measured may selectively vary between implementations. In one example implementation, the fluorophore sample (or blank sample) may be completely scanned across the entire excitation wavelength range before the blank sample (or fluorophore sample) is scanned. In another example implementation, the fluorophore sample may be measured at an excitation-emission wavelength pair and the blank sample may be measured at that same excitation-emission wavelength pair before incrementing the wavelengths in the wavelength pair.

Once the fluorophore sample and the blank sample have been scanned, the signal-to-background ratios are calculated for the excitation-emission wavelength pairs at step 66. The SB values may be determined according to the approach set forth above. If repeated measurements were taken, SN may be determined. At step 68, a map of the SB values (e.g., a heat map) may be generated. The SB values may map to a particular RGB color value for presentation of the color-coded SB values in a heat map. The RGB color values may be plotted on a 2D graph where the axes of the graph respectively correspond to the excitation and emission wavelength ranges. The map of SB values may then be analyzed, at step 70, to identify the maximum SB value and the excitation-emission wavelength pair associated with the maximum SB value. The maximum SB value corresponds to the optimal sensitivity level for the fluorophore.

As discussed above, the system for automatically determining the optimal excitation-emission wavelength pair of a fluorophore may display a user interface as part of a "wizard," macro, or script. FIGS. 3A-C are examples of user interface displays 72a-c that the system may present to a user as part of the "wizard," macro, or script.

Referring to FIG. 3A, an example of a user interface display 72a that prompts a user to input wavelength settings for an excitation-emission scan is shown. The user interface display 72a in the example shown includes respective input elements 74-76 for defining a desired excitation wavelength and emission wavelength. The user interface display 72a in FIG. 3A also includes control elements 78a-b for indicating whether the fluorophore is known or unknown. If a user indicates via control element 78a that the fluorophore is known, the user may enter the wavelength ROIs at input elements 74-76. If the user indicates via control element 78b that the fluorophore is unknown, a pre-scan may be initiated for automatically determining the excitation and emission wavelength ROIs.

In FIG. 3B, an example of a user interface display 72b that prompts a user to input the read settings for an excitation-emission scan is shown. The user interface display 72b in the example shown includes input elements 80a-b and 82a-b for specifying the start and end values for the excitation wavelength range (e.g., 360 nm-800 nm) and the start and end values for the emission wavelength range (e.g., 400 nm-850 nm). Additionally, the user interface display 72b in FIG. 3B includes an input element 84 for specifying the wavelength increment (e.g. 20 nm). As seen in FIG. 3B, a user may set additional read settings such as the reading height 86 above the microplate and the integration time 88.

Before the excitation-emission scan begins, a user interface display (not shown) may also prompt a user to select the carrier that holds the fluorophore sample and the carrier that holds the blank sample (i.e., the microplate well, cuvette, tube, slide, or other suitable carrier for holding the sample under test). The system may begin the excitation-emission scan once the user has input the wavelength settings, the read settings, and the selections of the microplate wells for the fluorophore sample and the blank sample.

Referring now to FIG. 3C, a user interface display 72c that presents the results of an excitation-emission scan is shown. As seen in FIG. 3C, the user interface display 72c in the example shown includes a heat map 90 that graphically represents the SB values as colors. In this example, low SB values are represented by a bluish color 92a and high SB values are represented by a reddish color 92b. The user interface in this example also includes a cursor 94 that may be used to inspect the heat map 90. A user may position the cursor 94 over various locations in the heat map 90, and the cursor may indicate the SB value and associated excitation and emission wavelengths for the location. In the example seen in FIG. 3A, the cursor 94 is positioned over the location in the heat map 96 that corresponds to the maximum SB value 98 (e.g., 270.6) and displays the associated excitation and emission wavelength pair. In this example, the maximum SB value 98 is associated with an excitation wavelength of 601 nm and an emission wavelength of 699 nm. Accordingly, the optimal excitation-emission wavelength pair for the fluorophore analyzed in FIG. 3C that correspond to the highest sensitivity level 100 for the fluorophore is 601 nm/699 nm.

As seen, the maximum SB value is determined for a fluorophore that corresponds to the optimum excitation-emission wavelength pair and the optimum sensitivity level for a fluorophore. The optimum excitation-emission wavelength pair for fluorophore sensitivity may also be considered as the optimum excitation-emission wavelength pair for fluorescence polarization, fluorescence lifetime, and time-resolved fluorescence. It will be understood that other independent parameters may additionally be optimized in order to optimize a fluorescence reading of a fluorophore. Additional parameters that may be optimized may include, for example, the selection of lab materials (e.g., a black, white, or transparent carrier) and the read time for each sample. For time-resolved fluorescence readings, additional parameters that may be optimized include, for example, the delay time and integration time for each excitation of the fluorophore.

Furthermore, the SB optimization approach set forth above may be applied to assays involving multiple fluorophores. Multiplexed assays may involve an analysis of a fluorophore mixture containing two or more fluorophores. In this example, the fluorophore measurements for the fluorophore mixture, F', at excitation-emission wavelength pairs may be used to calculate SB values, SB', for the fluorophore mixture $$\left(SB' = \frac{F' - B}{B}\right).$$

In this example, the heat map generated for the fluorophore mixture may show multiple SB peaks that respectively correspond to the multiple fluorophores in the fluorophore mixture. If, for example, the fluorophore mixture included two fluorophores each having a single maximum SB, the heat map for the fluorophore mixture may show two SB peaks. The user may thus identify a first optimum excitation-emission wavelength pair for the first fluorophore and a second optimum excitation-emission wavelength pair for the second fluorophore.

Moreover, the user may apply the SB optimization approach set forth above may be performed separately for each fluorophore in the fluorophore mixture prior to performing SB optimization for the fluorophore mixture itself—e.g., $$SB_1 = \frac{F_1 - B}{B}$$

for the first fluorophore and $$SB_2 = \frac{F_2 - B}{B}$$

for the second fluorophore. In this way, a user may obtain prior knowledge of the respective optimum excitation-emission wavelengths of the individual before mixing the fluorophores and identifying the optimum wavelength settings for the fluorophore mixture.

The SB optimization approach set forth above may also be applied when assessing interference from absorption or fluorescence of other compounds used in the assay. In cell-based assays, for example, NADH may interfere with fluorophore tracers excited in the UV range. In such circumstances, the SB optimization approach may be adapted to account for interference from other compounds. For example, instead of using a pure blank sample as a reference, a user may include an aliquot of the interfering compound in the blank sample. The fluorophore measurements, F, may be normalized using the measurements of the blank sample, B', that includes the interfering compound $$\left(SB' = \frac{F - B'}{B'}\right).$$

In this way, a single heat map may be generated that takes into account interference from other compounds used in the assay, and a user may identify the optimum excitation-emission wavelength pair for assays that include the interfering compound.

The SB optimization approach may additionally be used for analysis of fluorescence resonance energy transfer (FRET). FRET relates to assays for detecting dual fluorophore labels in which a donor fluorophore emits energy that is transmitted to an acceptor fluorophore in close proximity (e.g., approximately 10 nm) to the donor fluorophore. In some circumstances, the emission of energy from non-proximate aliquots of the donor fluorophore may interfere with the detection of the acceptor fluorophore. The approaches discussed above relating to multiplexing and interference may be employed to address any interference issues in a FRET analysis.

As mentioned above, the SB optimization procedure may be adapted for time-resolved fluorescence (TRF) in order to optimize parameters relevant to TRF such as, for example, the delay time and integration time for each excitation of the fluorophore. In this example adaptation, the settings for the excitation-emission wavelength pair are fixed and the scan varies the TRF parameters (e.g., the delay time and integration time). Accordingly, the maximum SB value in the heat map in this example thus corresponds to the optimum delay time-integration time pair at a particular excitation and emission wavelength.

It will be understood and appreciated that one or more of the processes, sub-processes, and process steps described in connection with FIGS. 1-2 may be performed by hardware, software, or a combination of hardware and software on one or more electronic or digitally-controlled devices. The software may reside in a software memory (not shown) in a suitable electronic processing component or system such as, for example, one or more of the functional systems, devices, components, modules, or sub-modules schematically depicted in FIG. 1. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module, which includes, for example, one or more microprocessors, general purpose processors, combinations of processors, DSPs, or ASICs. Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., a system 10 for automatically determining the optimal excitation-emission wavelength pair of a fluorophore in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A system for performing spectrofluorometry of a fluorophore sample comprising:
    an input module that receives user input corresponding to spectrofluorometer settings;
    a control module that transmits one or more control signals for controlling a spectrofluorometer during respective wavelength scans of the fluorophore sample and a blank sample, the one or more control signals provide for automatic execution of the wavelength scans over an excitation wavelength range and an emission wavelength range;

a signal-to-background determination module that automatically determines a plurality of signal-to-background ratios based on fluorescence measurements of the fluorophore sample and the blank sample received from the spectrofluorometer; and a signal-to-background analysis module that automatically determines the maximum signal-to-background ratio from the plurality of signal-to-background ratios; and a map generation module that generates a map of the plurality of signal-to-background ratios and wherein the map graphically presents the plurality of signal-to-background ratios as respective color-coded elements plotted on a graph; and the map generation module maps each signal-to-background ratio to a corresponding color.

2. The system of claim 1 wherein:
the control module pairs an excitation wavelength in the excitation wavelength range with an emission wavelength in the emission wavelength range to obtain an excitation-emission wavelength pair for a first iteration of one of the wavelength scans;
the control module transmits the one or more control signals to instruct the spectrofluorometer to measure the fluorophore sample or the blank sample at the excitation-emission wavelength pair; and
the excitation wavelength or the emission wavelength is incremented for a second iteration of the wavelength scan.

3. The system of claim 2 wherein:
the signal-to-background determination module receives the fluorescence measurements from the spectrofluorometer in response to receipt of the one or more control signals at the spectrofluorometer from the control module; and
the fluorescence measurements respectively quantify the fluorescent intensity of the fluorophore sample and the blank sample at the excitation-emission wavelength pair.

4. The system of claim 1 wherein the control module transmits one or more control signals to the spectrofluorometer instructing the spectrofluorometer to perform a low pre-scan of the fluorophore sample over an entire accessible wavelengths range for automatically identifying an excitation wavelength peak and an emission wavelength peak based on the accessible wavelengths range used during the pre-scan.

5. The system of claim 1 wherein:
the control module transmits one or more control signals to the spectrofluorometer instructing the spectrofluorometer to repeatedly scan the blank sample at a predetermined excitation-emission wavelength pair and at a predetermined number of cycles to obtain repeated measurements of the blank sample at the predetermined excitation-emission wavelength pair; and the signal-to-background determination module assesses noise in the blank sample based on the repeated measurements.

6. The system of claim 1 wherein the signal-to-background determination module respectively determines the plurality of signal-to-background ratios by normalizing the fluorescence measurements of the fluorophore sample at a predetermined excitation-emission wavelength pair based on the fluorescence measurements of the blank sample at the predetermined excitation-emission wavelength pair.

7. The system of claim 1 wherein:
the signal-to-background analysis module automatically determines the maximum signal-to-background ratio by calculating the absolute maximum signal-to-background ratio in the plurality of signal-to-background ratios; and an excitation-emission wavelength pair associated with the maximum signal-to-background ratio corresponds to an optimal sensitivity level for a fluorophore in the fluorophore sample.

8. A computer-implemented method of performing spectrofluorometry of a fluorophore sample comprising:
prompting for user input that corresponds to spectrofluorometer settings;
transmitting one or more control signals for controlling a spectrofluorometer during respective wavelength scans of the fluorophore sample and a blank sample, the one or more control signals provide for the automatic execution of the wavelength scans over an excitation wavelength range and an emission wavelength range;
automatically determining a plurality of signal-to-background ratios based on fluorescence measurements of the fluorophore sample and the blank sample received from the spectrofluorometer;
automatically determining the maximum signal-to-background ratio from the plurality of signal to background ratios; and
mapping each signal-to-background ratio to a corresponding color to obtain color-coded signal-to-background ratios; and generating a map of the one or more color-coded signal-to-background ratios wherein the map graphically presents the one or more color-coded signal-to-background ratios as respective color-coded elements plotted on a graph.

9. The computer-implemented method of claim 8 further comprising:
pairing an excitation wavelength in the excitation wavelength range with an emission wavelength in the emission wavelength range to obtain an excitation-emission wavelength pair for a first iteration of one of the wavelength scans;
transmitting one or more control signals that instruct the spectrofluorometer to measure the fluorophore sample or the blank sample at the excitation-emission wavelength pair; and incrementing the excitation wavelength or the emission wavelength for a second iteration of the wavelength scan.

10. The computer-implemented method of claim 9 wherein:
the fluorescence measurements from the spectrofluorometer are received in response to receipt of the one or more control signals at the spectrofluorometer; and
the fluorescence measurements respectively quantify the fluorescent intensity of the fluorophore sample and the blank sample at the excitation-emission wavelength pair.

11. The computer-implemented method of claim 8 further comprising:
transmitting one or more control signals to the spectrofluorometer instructing the spectrofluorometer to perform a pre-scan of the fluorophore sample over an entire accessible wavelengths range; and
automatically identifying an excitation wavelength peak and an emission wavelength peak based on the accessible wavelengths range used during the pre-scan.

12. The computer-implemented method of claim 8 further comprising:
transmitting one or more control signals to the spectrofluorometer instructing the spectrofluorometer to repeatedly scan the blank sample at a predetermined excitation-emission wavelength pair and at a predetermined number of cycles to obtain repeated measurements of the blank sample at the predetermined excitation-emission wavelength pair; and automatically assessing noise in the blank sample based on the repeated measurements.

13. The computer-implemented method of claim 8 further comprising:

automatically determining the plurality of signal-to-background ratios by normalizing the fluorescence measurements of the fluorophore sample at a predetermined excitation-emission wavelength pair based on the fluorescence measurements of the blank sample at the predetermined excitation-emission wavelength pair.

14. The computer-implemented method of claim 8 further comprising automatically determining the maximum signal-to-background ratio by calculating the absolute maximum signal-to-background ratio in the plurality of signal-to-background ratios and wherein an excitation-emission wavelength pair associated with the maximum signal-to-background ratio corresponds to an optimal sensitivity level for a fluorophore in the fluorophore sample.

15. A computer program product stored on a non-transitory computer readable medium for performing spectrofluorometry of a fluorophore sample, the computer program product having instructions stored therein which, when executed by a processing module of an electronic system, direct the electronic system to: prompt for user input that corresponds to settings of a spectrofluorometer by an input module; transmit by a control module one or more control signals for controlling the spectrofluorometer during respective wavelength scans of the fluorophore sample and a blank sample, the one or more control signals provide for the automatic execution of the wavelength scans over an excitation wavelength range and an emission wavelength range; automatically determine by a signal-to-background determination module a plurality of signal-to-background ratios based on fluorescence measurements of the fluorophore sample and the blank sample received from the spectra fluorometer; automatically determine by a signal-to-background analysis module the maximum signal-to-background ratio from the plurality of signal to background ratios; and map each signal-to-background ratio to a corresponding color to obtain color-coded signal-to-background ratio and generate a map of the one or more color-coded signal-to-background ratios by a map generation module, wherein the map graphically presents the one or more color-coded signal-to-background ratios as respective color-coded elements plotted on a graph.

16. The computer program product of claim 15 wherein the product further directs the electronic system to:

pair an excitation wavelength by the control module in the excitation wavelength range with an emission wavelength in the emission wavelength range to obtain an excitation-emission wavelength pair for a first iteration of one of the wavelength scans; transmit one or more control signals that instruct the spectrofluorometer to measure the fluorophore sample or the blank sample at the excitation-emission wavelength pair; and increment the excitation wavelength or the emission wavelength for a second iteration of the wavelength scan.

17. The computer program product of claim 15 wherein the product further directs the electronic system to:

transmit one or more control signals to the spectrofluorometer by the control module instructing the spectrofluorometer to repeatedly scan the blank sample at a predetermined excitation-emission wavelength pair and at a predetermined number of cycles to obtain repeated measurements of the blank sample at the predetermined excitation-emission wavelength pair; and automatically assess noise in the blank sample based on the repeated measurements.

\* \* \* \* \*